United States Patent [19]

Sokolovsky et al.

[11] 3,997,543
[45] Dec. 14, 1976

[54] PROCESS FOR PREPARING QUINUCLIDINE ENANTIOMERS

[76] Inventors: Mordechai Sokolovsky, 13 Rabina St.; Moshe Rehavi, 16 Reading St., both of Ramat Aviv; Saul Maayani, 7 Hahistadrut St., Givatayim, all of Israel

[22] Filed: Apr. 18, 1975

[21] Appl. No.: 569,282

[30] Foreign Application Priority Data

Apr. 24, 1974 Israel ................................. 44707

[52] U.S. Cl. ........................... 260/293.53; 424/267
[51] Int. Cl.$^2$ ....................................... C07D 211/42
[58] Field of Search ............................. 260/293.53

[56] References Cited

OTHER PUBLICATIONS

Kamilov, et al., Chem. Abst. 67: 10310y (1967).
Lieberman, et al., Chem. Abst. 67: 98897d (1967).
Ferlux, Fr. U. 5042, Chem. Abst. 71: 79711e (1969).
Agugini, et al., Chem. Abst. 70: 27540h (1969).
Karrer, Org. Chem. 2nd Ed. (1946) pp. 92–102.

*Primary Examiner*—Natalie Trousof
*Assistant Examiner*—C. M. S. Jaisle
*Attorney, Agent, or Firm*—Browdy and Neimark

[57] ABSTRACT

A new composition of matter, (+) 3-acetoxy- quinuclidine and its salts, ophthalmic compositions comprising this compound or any of its physiologically acceptable salts in a suitable carrier such as a phosphate buffer, and a process of preparation of the active ingredients, which comprises esterifying quinuclidinol so as to obtain racemic 3-lower-alkoxy quinuclidine, subjecting same to enzymatic hydrolysis by a cholinesterase so as to selectively hydrolyze the (−) isomer, separating the unchanged (+) lower-alkoxy quinuclidine, hydrolyzing the latter and esterifying it to the desired compound. Amongst various homolophes the preferred compound is (+)3-acetoxy quinuclidine as this is pharmaceutically the most potent one.

2 Claims, No Drawings

PROCESS FOR PREPARING QUINUCLIDINE ENANTIOMERS

BACKGROUND OF THE INVENTION

The present invention relates to a novel composition of matter. More particularly, it relates to a novel enantiomer of a known compound which is characterised by unexpected advantageous pharmacological properties and to pharmaceutical preparations containing this isomer as active ingredient. Other and further aspects of the present invention will become apparent hereinafter.

Hitherto compounds belonging mainly to two families of chemical compounds are used for the treatment of glaucoma:
a. Cholinesterase inhibitors like eserine (physostigmine) and phospholine;
b. Acetylcholine like drugs, such as pilocarpine and aceclidine.

One of the drawbacks of pilocarpine is the lack of stability of solutions of same. Furthermore, it is necessary to resort to repeated topical applications every few hours in order to reduce the intraoccular pressure due to glaucoma.

Aceclidine is suited for the treatment of glaucoma, and this is the racemic form of 3-acetoxy-quinuclidine. According to the invention, it has been found that the (+) form of 3acetoxy-quinuclidine has pronounced advantageous pharmacological properties in comparison with the racemic form. The (+) form decreases effectively the intraoccular pressure due to glaucoma, and the effect lasts for comparatively prolonged periods of time. It is one of the important advantages of the (+) isomer that it has a comparatively long shelf life. While that of solutions of pilocarpine is about 1 to 2 months, that of solutions of the (+) isomer is at least 6 months.

SUMMARY OF THE INVENTION:

According to the present invention an enzymatic process is used in the process of preparation of the desired isomer.

The resolution of racemic (+) 3-quinuclidinol by a chemical method was described in literature by Kaiser, JACS 74 (1952) 2215 and by Kalir et al, Israel J. Chem 9 (1971) 267. The chemical processes are quite complicated and give comparatively low yields.

According to the present invention there is provided a novel process for the preparation of (+) 3-acetoxyquinuclidine in high yields; there is provided the (+) isomer in substantially pure form and there are provided novel pharmaceutical preparations, adapted for the treatment of glaucoma, which contains only this isomer, as active ingredient.

According to the present invention there is provided a novel process for the preparation of (+) 3-acetoxyquinuclidine which comprises esterifying racemic quinuclidinol with a suitable acid anhydride, such as butyric anhydride to yield racemic 3-alkanoyloxy quinuclidine, in this case 3-butyroxy quinuclidine. This ester is subjected to specific enzymatic hydrolysis by a suitable esterase, such as butyryl cholinesterase (obtained from horse serum, EC 3118), which is effected by incubation at a pH of about 7 and at a temperature of 40° C during 48 hours. This enzymatic process results in the practically complete hydrolysis of only the (−) isomer to the corresponding alcohol, quinuclidine, whereas the (+) isomer remains practically unchanged.

The resulting two compounds are separated by conventional techniques, and separation on a column of neutral alumina by elution with chloroform was found to be suitable. The chloroform is removed, and the separated (+) butyroxy quinuclidine is hydrolyzed quantitatively to yield the free amino alcohol (+) quinulclidinol, which is crystallized from acetone. Esterification of this isomer yields the desired ester. Esterification by means of acetic anhydride yields the desired (+) 3-acetoxy quinuclidinol. The desired isomer can be obtained in a form suitable for the intended application, as for example in the form of a salt like hydrochloride which can be obtained from anhydrous ether. Yields of the enzymatic separation are much higher (of the order of 60 per cent calculated on the isomer content) than those of the chemical methods.

DESCRIPTION OF THE PREFERRED EMBODIMENT:

The desired compound was prepared as follows:
Racemic quinuclidinol (20 g) was inserted with 65 ml pyridine into a glass vessel of 250 ml volume, and 31 ml butyric anhydride were added. After refluxing during 2 hours the pyridine was distilled off (20° C, 1 mm Hg), after which the excess of butyric anhydride was distilled off at 68° C, 1 mm Hg. The ester was distilled off at 96° C, 1 mm Hg, yield 80 percent calculated on the quinuclidinol.

The enzymatic hydrolysis was effected as follows:
To a glass vessel of 1 liter volume there was added 10 g of racemic 3-butyroxy quinuclidine, 52 ml 1 N HCl, 100 ml 0.02 M phosphate buffer, and the pH was adjusted to pH 7.0. The volume was adjusted to 500 ml by the addition of water and the reaction mixture was warmed to 40° C.

There was added a quantity of 50 mg butyrylcholin esterase, 4 units/mg protein and the pH was adjusted from time to time to pH 7.0 by the addition of 0.1 N NaOH. At the completion of the enzymatic process the decrease of pH ceases. The reaction was complete after 36–48 hours.

The reaction mixture was acidified to pH 6.0 and water was removed under reduced pressure at 40° C, 1 mm Hg. It was extracted with 4 portions of 100 ml each of methanol and the methanolic phase was filtered, and the methanol was evaporated.

A 3 cm × 30 cm of neutral alumina (Merck, activity I) was loaded with a chloroformic suspension of 50 ml. The quantity of alumina was 250 g. The aminoester was flushed from the column by means of chloroform at a flow rate of 4 ml/minute, while the amino-alcohol remains on the column. The aminoester starts leaving the column after 300 ml chloroform and is collected in a total volume of 800 ml. At the end of the elution of the aminoester, the column is flushed with methanol until the elution of the amino-alcohol starts. The elution of this starts after about 300 ml methanol and the total quantity is collected in a volume of about 800 ml.

The chloroform is evaporated and the residue is dissolved in 50 ml water and 10 ml 5 N NaOH. After evaporation of the water at 40° C, 1 mm Hg, the residue is extracted 4 times with portions of 50 ml each of chloroform, the solution is filtered and dried over sodium sulfate. After evaporation of the chloroform crystalline (+) quinuclidinol is obtained, after recrystallization from acetone: M.P. 215°–217° C, $[\alpha]_{25}^{D} = +46°$ (1N HCl, C=2), yield: 60 percent.

The thus obtained (+) quinuclidinol was esterified with acetic anhydride to yield in a quantitative manner the desired novel (+) 3-acetoxy quinuclidine. The hydrochloride was obtained from a solution of hydrogen chloride in anhydrous ether, M.P. = 175° C.

In a similar manner various aminoesters were prepared and the physical data are given in Table I.

The ACh-like activity of various compounds were tested on guinea pig ileum according to the Edinburg staff method. Pharmaceutical experiments on isolated preparations, E & S Livingstone, London (1970), the results are given in Table II.

The tests were carried out with four groups each of six guinea pigs. The (+) enantiomer (HCl salt) was found to be the strongest agonist and was blocked by $3 \times 10^{-8}$M atropine. The dose-response curves obtained with all the studied compounds were found to be parallel to that of ACh and to reach the same maximum response value.

The miotic activity of the two (+) and (−) enantiomers is given in Tables III and IV. This was tested on human volunteers, and each of the Tables represents average values of six different persons. Solutions of the concentration indicated in the Tables were applied locally, these were solutions in 0.1 M phosphate buffer, pH 7.0.

Data on pupil diameter and intraoccular pressure after treatment with pilocarpine and with (+) 3-acetoxy quinuclioine are given in Tables V and VI, respectively.

The antimydriatic activity of (+) 3-acetoxy quinuclidine was tested on mice eyes and on human eyes, the results are given in Tables VII and VIII respectively. Mydriasis developed after application of $10^{-2}$M phencyclidine hydrochloride, pH 7.4 in 0.1 M phosphate buffer. One drop was applied per eye. The tests were conducted on four groups of six mice each and on six human volunteers. Average values are given. As regards Table VII it is pointed out that when phosphate buffer is applied to the eye, the value is also >15 minutes, and thus the values of >15 are equivalent to blank tests.

Various physiologically acceptable salts were tested. Any salt having an adequate solubility in aqueous solutions, and especially in phosphate buffer, can be used. There were tested: the sulfate, the nitrate, the salicylate, acetate etc. The anion does not seem to have any influence on the activity of the compound.

The stability of solutions of (+) 3-acetoxy quinuclidine was tested. Solutions were prepared which contained concentrations of the active ingredient of 1 and 2 percent by weight in 0.1M phosphate buffer, pH 7.0, these were stored for various periods. It was found that after storage of 6 months no perceptible deterioration had taken place. This composition was used for the tests.

From the above it is clear that (+) acetoxy quinuclidine is an effective agent for the treatment of glaucoma. It is also an effective antimydriatic, and as such can be used for treating persons after the application of mydriatics used for eye examinations and the like.

The (+) 3-acetoxy quinuclidine can be used as such or as a physiologically acceptable salt, like hydrochloride or the like. Its activity as active ingredient in pharmaceutical compositions is much higher than that of the corresponding racemic mixture and much higher than would be expected from an arithmetic computation of the content in the racemic mixture. It seems that this is due to the fact that when a racemic mixture is used, the ineffective (−) component occupies certain sites, and prevents molecules of the active (+) isomer from exerting their activity at such sites.

It is clear that the novel enantiomer can be used as ingredient of varying pharmaceutical compositions of matter, either alone, or in combination with other active ingredients.

TABLE I

AMINO ESTERS DERIVED FROM 3-QUINUCLIDINOL

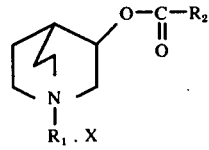

| Amino alcohol | Amino Ester R₁ | R₂ | X | B.P. (mm/Hg) M.P. (° C) | $[\alpha]_{25}^D$ (1) |
|---|---|---|---|---|---|
|  | H | CH₃ | Cl | 118/20 | — |
| (±) | CH₃ | CH₃ | I | 165 | — |
| (+) | H | CH₃ | Cl | 175 | 14.3 |
|  | CH₃ | CH₃ | I | 201 | 11.5 |
| (−) | H | CH₃ | Cl | 175 | 16.3 |
|  | CH₃ | CH₃ | I | 201 | 11.5 |
| (±) | H | C₃H₇ | Cl | 140/20 | — |
|  | CH₃ | C₃H₇ | I | 195 | — |

(1) in 1N HCl (c = 1.5).

TABLE II

Muscarinic Activity of 3-AQ Derivatives on the isolated Smooth Muscle

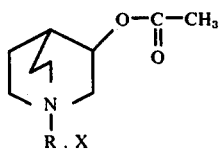

| Amino Alcohol | R | X | ED₅₀ (M) | EPMR |
|---|---|---|---|---|
| (±) | H | Cl | $7 \cdot 10^{-7}$ | 20 |
| (+) | H | Cl | $1.5 \cdot 10^{-7}$ | 25 |
| (−) | H | Cl | $3 \cdot 10^{-6}$ | 100 |
| (±) | CH₃ | I | $7 \cdot 10^{-5}$ | >1000 |
| (+) | CH₃ | I | $2 \cdot 10^{-5}$ | 600 |
| (−) | CH₃ | I | $8 \cdot 10^{-5}$ | >1000 |
| Acetylcholine |  |  | $3 \cdot 10^{-8}$ | 1 |

EPMR = Equipotent molar ratio

TABLE III

Miotic Activity of (+) 3 AcQ . HCl (Human Eyes)
Concentration (in phosphate buffer)

| 0.5 % | | 0.25 % | | 2.0 % | |
|---|---|---|---|---|---|
| Time (min) | Pupil Diam. (mm) | Time (min) | Pupil Diam. | Time (min) | Pupil Diam. |
|  | R    L |  | R    L |  | R    L |
| 0 | 2.5  2.5 | 0 | 4.5  4.5 | 0 | 2.5  3.0 |
| 20 | 1.2  1.2 | 7 | 4.5  4.5 | 20 | 1.0  1.0 |
| 40 | 1.0  1.0 | 18 | 3.0  3.0 | 45 | 0.8  0.8 |
| 70 | 1.0  1.0 | 30 | 2.7  2.7 | 300 | 0.8  0.8 |
| 105 | 1.0  1.0 | 45 | 2.7  2.7 |  |  |
| 150 | 1.0  1.0 | 90 | 2.0  2.0 |  |  |
| 200 | 1.0  1.0 | 180 | 2.7  2.7 |  |  |
| 230 | 1.0  1.0 | 300 | 2.5  2.5 |  |  |
|  |  | 390 | 3.5  3.5 |  |  |

L: left eye, R: right eye

TABLE IV

Miotic Activity of (−) 3 AcQ.HCl (Human Eyes)

| Time (Min.) | Conc: 0.5% Pupil Diameter (mm) | | 1.0% | | 2.0% | |
|---|---|---|---|---|---|---|
| | R | L | R | L | R | L |
| 0 | 4.5 | 4.5 | 4.5 | 4.5 | 4.5 | 4.5 |
| 6 | 4.0 | 4.5 | 4.0 | 4.0 | 4.0 | 4.0 |
| 18 | 4.0 | 4.0 | 3.5 | 3.5 | 3.7 | 3.7 |
| 30 | 3.0 | 3.2 | 3.5 | 3.5 | 3.5 | 3.5 |
| 45 | — | — | 4.0 | 4.0 | 3.6 | 3.5 |
| 60 | — | — | 4.0 | 4.0 | 4.0 | 4.0 |
| 80 | 4.5 | 4.5 | 4.5 | 4.5 | 4.5 | 4.5 |

TABLE VII

Antagonistic Activity of 3-AcQ Derivatives to Mydriasis induced by Phencyclidine in Mice Eyes

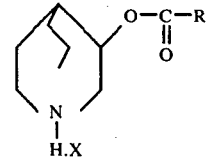

| Amino Alc. | R | X | Reversal of Mydriasis Conc. (M) | Time (min) |
|---|---|---|---|---|
| (±) | H | Cl | $2 \cdot 10^{-1}$ | 5 |
| | H | Cl | $2 \cdot 10^{-2}$ | 10 |
| | H | Cl | $2 \cdot 10^{-3}$ | >15 |
| (+) | H | Cl | $2 \cdot 10^{-1}$ | 4 (a) |
| | H | Cl | $2 \cdot 10^{-2}$ | 7 |
| | H | Cl | $2 \cdot 10^{-3}$ | >15 |
| (−) | H | Cl | $2 \cdot 10^{-1}$ | >15 |
| (±) | CH₃ | I | $2 \cdot 10^{-1}$ | >15 |

(a) acute miosis developed after 4 minutes

TABLE V

Pupil Diameter and Intraoccular Pressure after treatment with Pilocarpine

| Time (min) | Intraoccular pressure (mmHg) | | Pupil Diameter (mm) | |
|---|---|---|---|---|
| | L | R | L | R |
| 0 | 31 | 33 | 2.8 | 2.8 |
| 30 | 24 | 25 | 1.2 | 1.2 |
| 90 | 24 | 26 | 1.2 | 1.2 |
| 180 | 26 | 29 | 1.2 | 1.2 |
| 240 | 26 | 28 | 1.2 | 1.2 |
| 300 | 24 | 26 | 1.5 | 1.5 |

TABLE VI

Intraoccular Pressure after (+)3-AcQ.HCl treatment

| Time (min) | Conc: 0.5% (in mmHg) | | Time (min) | 2.0%-Conc. (in mmHg) | |
|---|---|---|---|---|---|
| | L | R | | L | R |

TABLE VI-continued

Intraoccular Pressure after (+)3-AcQ.HCl treatment

| Time (min) | Conc: 0.5% (in mmHg) | Time (min) | 2.0%-Conc. (in mmHg) |
|---|---|---|---|
| 0 | 28 | 30 | 0 | 24 | 24 |
| 20 | 28 | 30 | 20 | 21 | 22 |
| 40 | 26 | 27 | 45 | 21 | 22 |
| 70 | 23 | 23 | 105 | 21 | 22 |
| 105 | 21 | 21 | 180 | 18 | 20 |
| 150 | 21 | 23 | 240 | 16 | 23 |
| 200 | 25 | 25 | 300 | 18 | 25 |
| 230 | 22 | 23 | 360 | 21 | 27 |

TABLE VIII

Antimydriatic Activity of (+) 3-AcQ.HCl (Human Eyes)

| Time after mydriatic Treatment (in min.): Concentration: | 25 0.5% | 50 0.25% | |
|---|---|---|---|
| Time after (+)AcQ. HCl (in min.): | mm | Time after (+)AcQ.HCl in minutes | mm |
| & 0 | 8.2 | & 0 | 8.0 |
| 15 | 6.8 | 20 | 6.7 |
| 22 | 3.8 | 40 | 4.5 |
| 45 | 3.0 | 70 | 4.0 |
| 80 | 2.3 | 180 | 3.5 |
| 120 | 2.3 | 255 | 3.5 |
| 220 | 1.8 | | |
| 300 | 1.6 | | |

(mm pupil diameter)
L: left eye
R: right eye

We claim:
1. In a process for the preparation of (+) enantiomers of the general formula wherein R designates lower alkyl of up to and including 3 carbon atoms, and X designates a physiologically acceptable anion, the step which comprises esterifying racemic 3-quinuclidinol by conventional means so as to obtain racemic 3-lower alkanoyloxy quinuclidine, subjecting the thus obtained product to enzymatic hydrolysis by a suitable cholinesterase, so as to selectively hydrolyse the (−) isomer, separating the unchanged (+) 3-lower-alkanoyloxy quinuclidine, hydrolyzing the (+) 3-lower-alkanoyloxy quinuclidine to obtain (+)-3-quinuclidinol.

2. A process as claimed in claim 1 wherein the first esterification is effected with butyric anhydride, and the enzymatic hydrolysis is effected by means of butyryl cholinesterase (EC 3118).

* * * * *